United States Patent [19]

Spingler

[11] Patent Number: 5,479,980
[45] Date of Patent: Jan. 2, 1996

[54] METHOD AND DEVICE FOR FORMING DRILLED NEEDLE BLANKS

[75] Inventor: Rolf A. Spingler, Jestetten, Germany

[73] Assignee: United States Surgical Corporation, Norwalk, Conn.

[21] Appl. No.: 324,548

[22] Filed: Oct. 18, 1994

Related U.S. Application Data

[63] Continuation of Ser. No. 51,456, Apr. 21, 1993, Pat. No. 5,384,945.

[51] Int. Cl.$^6$ ............................. B21G 1/00; B23P 23/06
[52] U.S. Cl. ................................. 163/5; 29/33 R; 163/1
[58] Field of Search .................... 29/33 R, 407, 29/517, 414, 557, 558; 163/1, 2, 3, 5; 219/121.68, 121.66

[56] References Cited

U.S. PATENT DOCUMENTS

| | | |
|---|---|---|
| Re. 1,821 | 11/1864 | Sands . |
| 641,627 | 1/1900 | Heusch . |
| 963,987 | 7/1910 | Bohin . |
| 1,951,841 | 3/1934 | Roberts . |
| 3,565,131 | 2/1971 | Kaestner . |
| 3,735,656 | 5/1973 | Strandell et al. . |
| 3,994,445 | 11/1976 | Tarulli . |
| 4,060,885 | 12/1977 | Hoffman et al. . |
| 4,064,729 | 12/1977 | Homery . |
| 4,072,041 | 2/1978 | Hoffman et al. . |
| 4,177,843 | 12/1979 | Sarver . |
| 4,235,362 | 11/1980 | Hubenko . |
| 4,302,996 | 12/1981 | Wilhelm . |
| 4,310,032 | 1/1982 | Normandin . |
| 4,335,758 | 6/1982 | Williams . |
| 4,355,526 | 10/1982 | Miles . |
| 4,391,307 | 7/1983 | Levi et al. . |
| 4,422,583 | 12/1983 | Maxner et al. . |
| 4,464,916 | 8/1984 | Grew et al. . |
| 4,464,919 | 8/1984 | Labbe . |
| 4,470,330 | 9/1984 | Lindell . |
| 4,501,312 | 2/1985 | Matsutani . |
| 4,534,499 | 8/1985 | Cox et al. . |
| 4,541,470 | 9/1985 | Pavel . |
| 4,572,421 | 2/1986 | Hug et al. . |
| 4,610,281 | 9/1986 | Fuchs et al. . |
| 4,629,105 | 12/1986 | Grenon . |
| 4,638,558 | 1/1987 | Eaton . |
| 4,672,734 | 6/1987 | Kawada et al. . |
| 4,688,412 | 8/1987 | Hoffman . |
| 4,866,970 | 9/1989 | Castiglioni . |
| 4,901,722 | 2/1990 | Noguchi . |
| 4,910,377 | 3/1990 | Matsutani et al. . |
| 4,920,776 | 5/1990 | Denzler . |
| 4,923,133 | 5/1990 | Zaman et al. . |
| 5,001,323 | 3/1991 | Matsutani et al. . |
| 5,012,066 | 4/1991 | Matsutani et al. . |
| 5,080,295 | 1/1992 | Raggio et al. . |
| 5,109,690 | 5/1992 | Taniguchi et al. . |
| 5,137,223 | 8/1992 | Brandon et al. . |
| 5,139,206 | 8/1992 | Butler . |
| 5,384,945 | 1/1995 | Spingler . |
| 5,411,613 | 5/1995 | Rizk et al. ............................ 163/5 X |

FOREIGN PATENT DOCUMENTS

| | | |
|---|---|---|
| 0530410 | 3/1993 | European Pat. Off. . |
| 912675 | 8/1946 | France . |
| 552242 | 5/1932 | Germany . |
| 2413433 | 10/1974 | Germany . |
| 2947706 | 7/1981 | Germany . |
| 60-35151 | 8/1985 | Japan ............................... 39/33 R |
| 62-101236 | 5/1987 | Japan . |
| 3-80869 | 4/1991 | Japan . |
| 3118050 | 5/1991 | Japan . |
| 3519 | of 0000 | United Kingdom . |
| 1424953 | 2/1976 | United Kingdom . |

*Primary Examiner*—William Briggs

[57] ABSTRACT

An apparatus for preparing drilled needle blanks from a spool of coiled stock wire may include a laser for drilling a bore in the end of the stock wire and a cutting device for cutting the drilled wire into needle blanks.

18 Claims, 7 Drawing Sheets

FIG. 9

METHOD AND DEVICE FOR FORMING DRILLED NEEDLE BLANKS

This is a continuation of U.S. application Ser. No. 08/051,456 filed Apr. 21, 1993 U.S. Pat. No. 5,384,945.

FIELD OF THE INVENTION

This invention relates to processes and apparatus for forming needles. More particularly, this invention relates to processes and apparatus for forming needle blanks useful in forming surgical needles, the needle blanks having one end of the blank drilled for attachment of a suture to the needle.

BACKGROUND OF THE INVENTION

The production of needles involves many processing steps and different types of machinery to perform each step. The accuracy and repeatability of the various processes become more critical in the preparation of high quality surgical needles from raw stock. Some of the processes involved in the production of surgical grade needles include straightening spooled wire stock, cutting a length of stock wire to form a needle blank, tapering or grinding points on one end of the blank, providing a bore for receiving suture thread at the other end of the blank, flat pressing a portion of the needle barrel to facilitate easier grasping by surgical instrumentation, and curving the needle where curved needles are desired.

Normally, each processing step is performed by a different piece of machinery. This requires that the needle blanks be manually transferred from one piece of machinery to another as sequential processing steps are carried out. The transfer step increases the time and manpower necessary for needle production.

Generally, there are numerous ways to drill or cut the hole in the end face of a needle blank. For example, the hole may be made by drill machining, electric discharge machining, laser beam machining, electron beam machining and the like. With the advent of microsurgical procedures, surgical sutures have become increasingly smaller in size, thus requiring increased precision in needle production techniques and making it more complex and costly to manufacture the surgical needles. In particular, one aspect of surgical suture manufacturing which has become more difficult and complex for small diameter needles is drilling the hole in the needle blank. The small diameter needle blanks must be presented to the bore-forming device with extreme precision to ensure centrality of the bore formed therein. In addition, as the diameter of the wire decreases, as a general rule so does the length of the needle. Precise handling of short, very fine needle blanks without causing damage to the needle blank is quite difficult to achieve.

A common procedure for making a hole in a surgical needle utilizes laser or electron beam machining. In order to utilize these methods in a production environment, techniques have been developed to sequentially present a series of needle blanks to the beam for cutting. One such technique includes presenting the blank needle from a rotary spool which rotates to sequentially prevent an end face of a needle blank in line with the focal plane of the laser or electron beam. However, one drawback to this technique is that the rotating spool must stop before the beam is impinged on the needle. In order to operate properly the spool must come to a reset at precisely the same portion aligned with the focus point of the beam. If the needle in the rotating spool is not precisely aligned with the focus point of the beam, the hole created in the needle blank would be off center, thereby reducing the accuracy of the production process and ultimately resulting in increased defective quantities of needles. Currently, rotary spool systems are unable to obtain the precise positioning required for laser or electron beam machining. This lack of precision is magnified as the speed in which the blank needle is presented increases. As a result, the reliability and accuracy of rotary spool feeding systems is unacceptable in a high volume production environment.

Another technique utilized has been to bundle needle blanks in a container, digitize an image of the needle blank faces in the bundle and move the laser or electron beam to focus sequentially on each needle blank before firing the beam. These types of beam machining devices also have drawbacks, such as the need to optically determine where each needle blank is and then move the beam to coincide with the longitudinal axis at the center of the needle blank. Such systems are complex and require additional steps in order to determine the precise position of each needle blank. As a result, the speed of producing sufficient quantities to satisfy production needs is decreased.

Therefore, a need exists for an apparatus for producing drilled needle blanks in an accurate and reproducible manner at high speeds. In addition, a need exists for an apparatus for producing drilled needle blanks in a cost effective manner which does not require manual transporting of the needle blanks between different pieces of machinery.

SUMMARY OF THE INVENTION

The present invention relates to an apparatus for preparing drilled needle blanks from a spool of coiled stock wire. The apparatus of this invention includes means for straightening the stock wire, means for forming a suture attachment portion at a first end of said stock wire and means for cutting said stock wire to a predetermined length to form a drilled needle blank. The apparatus may also include sensing means for regulating the speed at which the stock wire advances through the apparatus.

BRIEF DESCRIPTION OF THE DRAWINGS

The features of the present invention will become more readily apparent and may be understood by referring to the following detailed description of an illustrative embodiment of the invention, taken in conjunction with the accompanying drawings, in which.

DETAILED DESCRIPTION OF THE PREFERRED EMBODIMENTS

Figure 1:
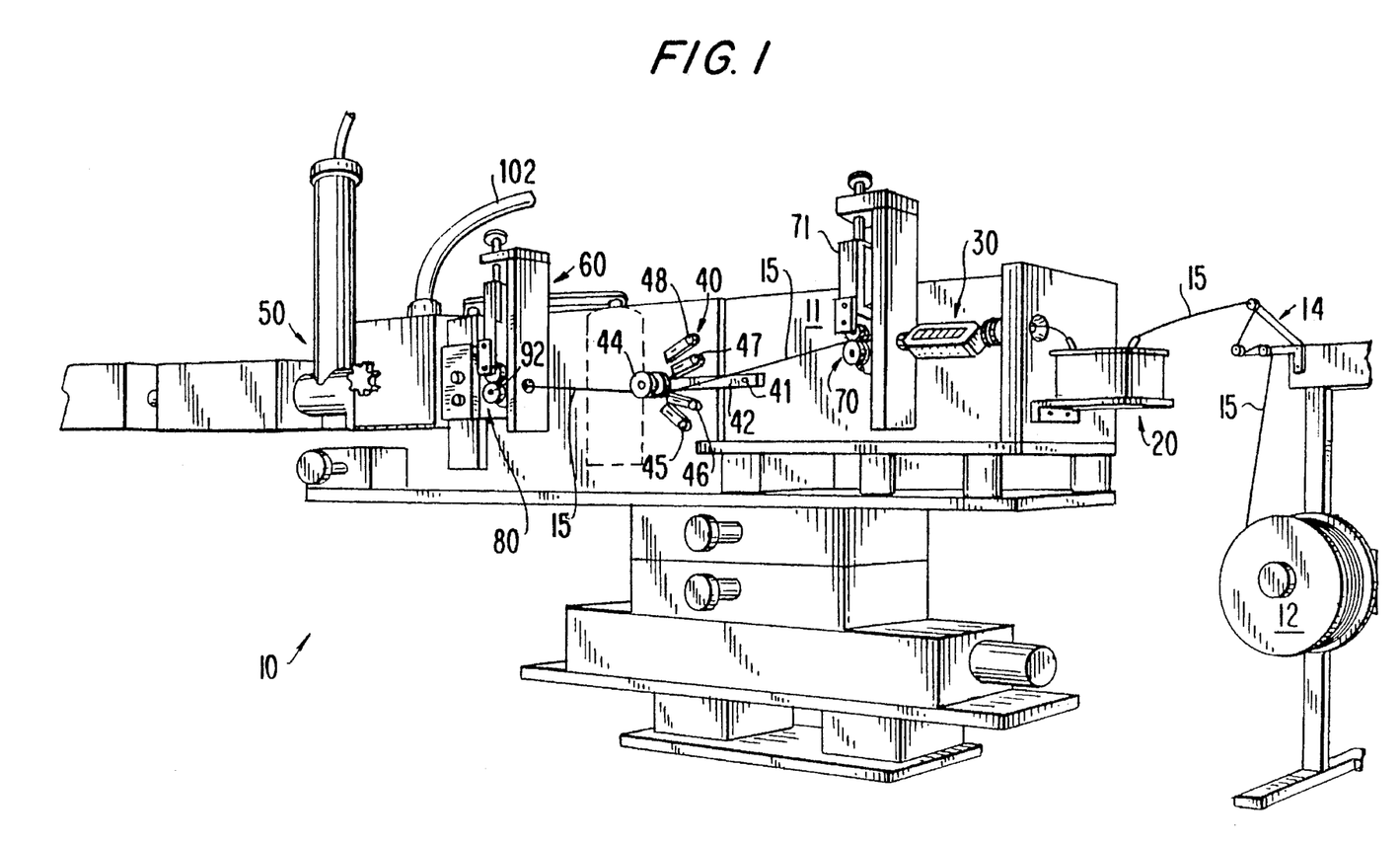
FIG. 1 is a perspective view of a needle blank forming apparatus in accordance with the present invention.

Referring now in detail to the drawings, in which like reference numerals identify similar or identical elements throughout the several views, FIG. 1 illustrates a needle blank forming apparatus 10 in accordance with the present invention. Stock wire 15 provided on spool 12 passes through a cleaning station 20, a straightening station 30, a sensing station 40, and a cutting station 60. The lead end 16 of the stock wire 15 extends out of cutting station 60 and is presented to a drilling system 50. Two pair of drive mechanisms 70 and 80 advance the stock wire through the needle blank forming apparatus 10.

Figure 2:
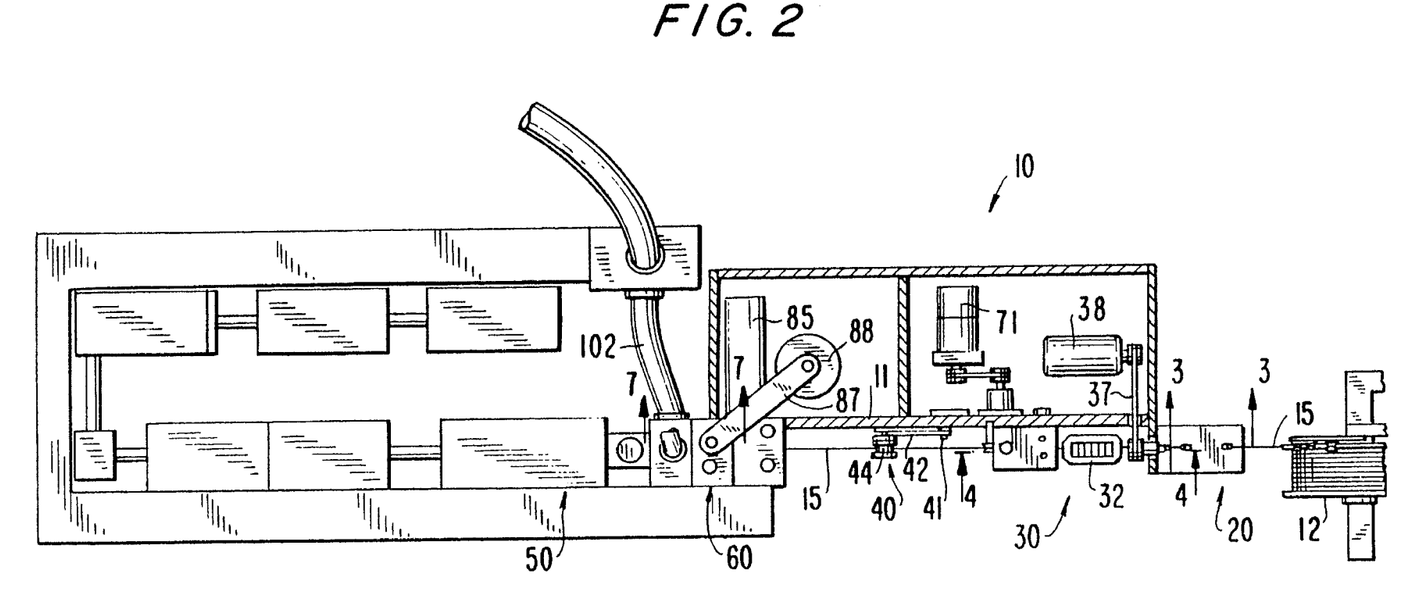
FIG. 2 is a top view, partially in cross-section, of the needle blank forming apparatus of FIG. 1.

As best seen in FIGS. 1 and 2, stock wire 15 is threaded through tensioning means 14. The tensioning means 14 is of a conventional type and maintains a constant tension on stock wire 15 to facilitate smooth passage of the wire through apparatus 10 and to prevent stock wire 15 from unraveling from spool 12.

Figure 3:
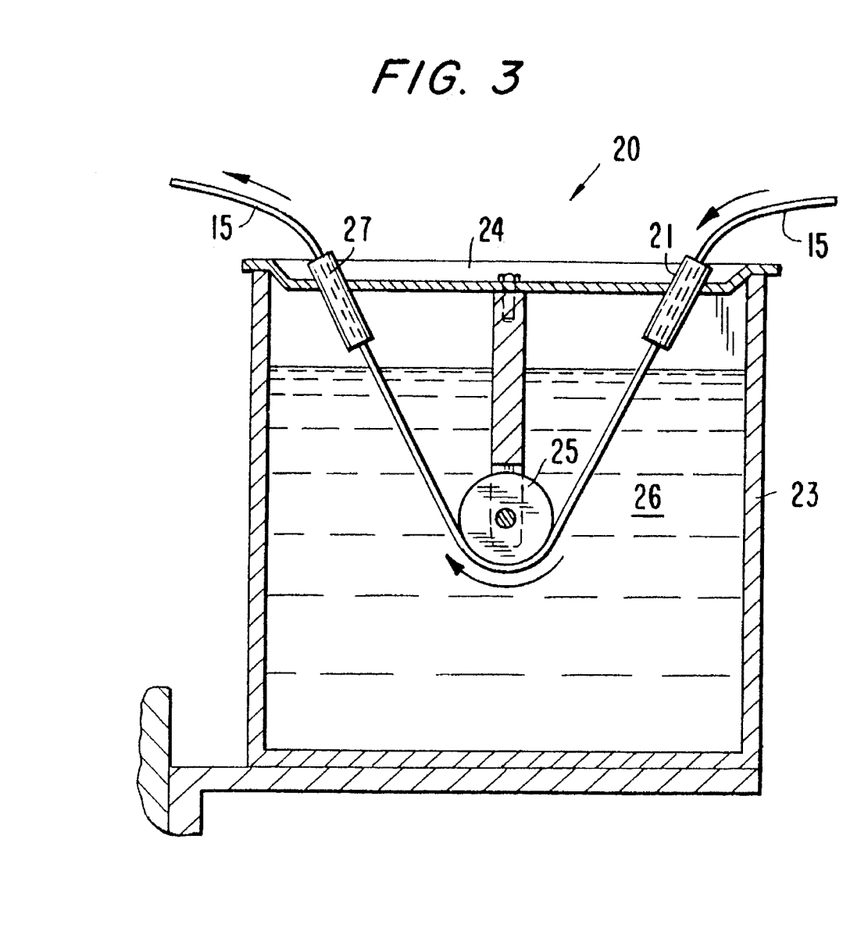
FIG. 3 is a cross-sectional view along line 3—3 of FIG. 2.

The stock wire is then passed through cleaning station 20. The cleaning station 20 may be of a conventional type and is preferably an ultrasonic cleaner. As seen in FIG. 3, stock wire 15 passes through inlet guide tube 21, around roller 25 and through outlet guide tube 27. Tank 23 of the cleaning station 20 is filled with cleaning solution 26. Guide tubes 21, 27 and roller 25 may be mounted to a removable lid 24 to facilitate loading the stock wire 15 through the cleaning station 20.

Figure 4:
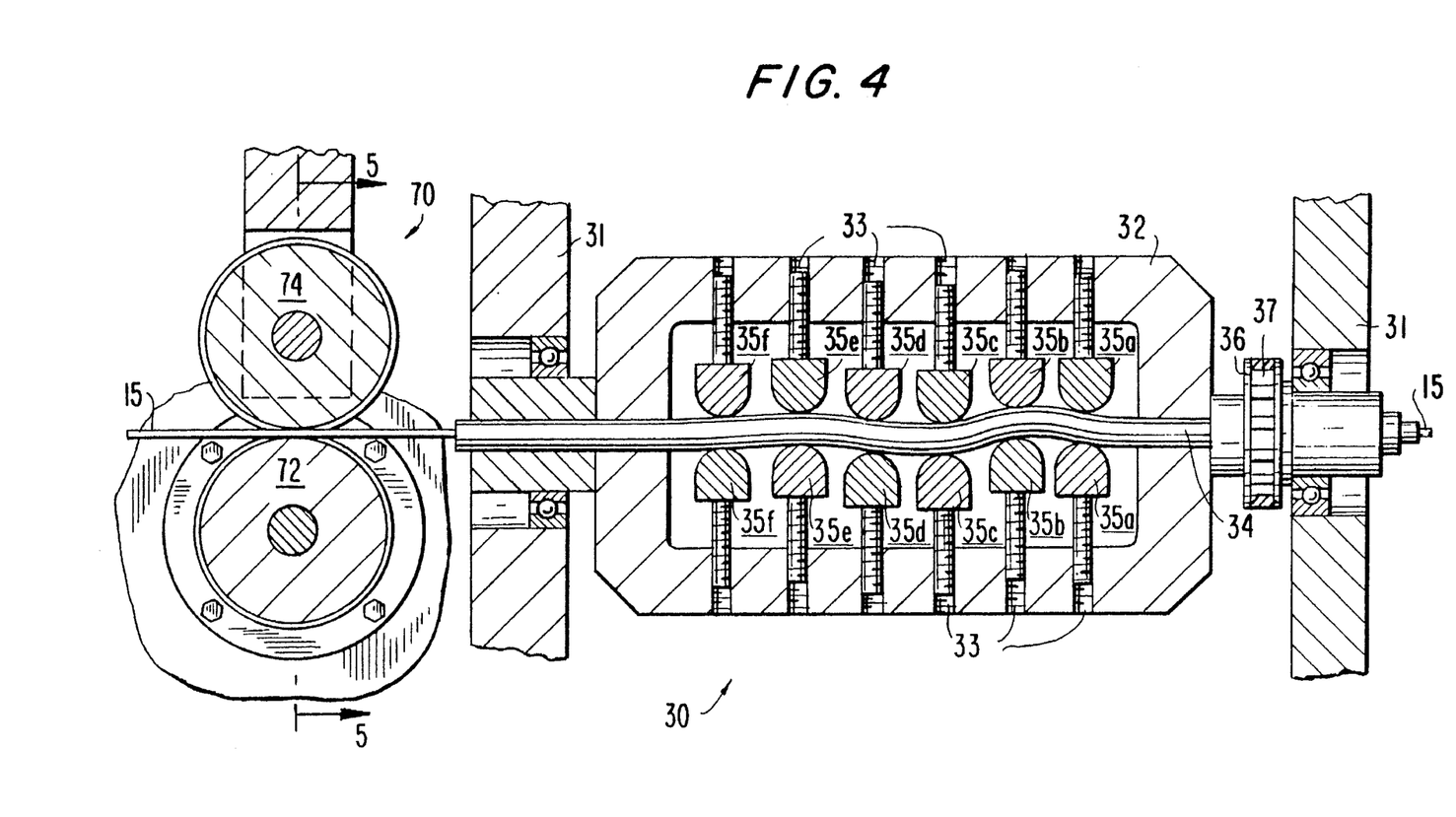
FIG. 4 is a cross-sectional view along line 4—4 of FIG. 2.

After exiting from cleaning station 20, stock wire 15 passes to straightening station 30. As shown in FIG. 4, straightening station 30 includes a housing 32 rotatably mounted to a frame 31 and a series of pairs of die elements 35 adjustably mounted to housing 32. The housing may have anywhere from three to twenty or more pairs of die elements mounted therein. A flexible guide tube 34 is adapted to receive the stock wire 15 and extends through the housing 32 between each pair of dies 35. Guide tube 34 may be made of any flexible material such as, for example polytetrafluoroethylene. Die elements 35 engage and flex guide tube 34. A drive motor 38 is operatively connected to housing 32 via belt 37 which passes around pully 36. Drive motor 38 imparts continuous rotational motion to the straightener housing 32 such that guide tube 34 is engaged by one or more pairs of die elements 35 from an infinite number of directions. Preferably, the housing 32 is rotated at a speed in the range 1500 to 4000 rpm.

Die elements 35 are disposed on opposed sides of the longitudinal axis defined by straightener housing 32 as shown. Each die element 35 is mounted within a respective mounting channel 33 and may be positioned to intersect the longitudinal axis defined by straightener housing 35 and engage guide tube 34 to alter the path of the guide tube as shown. The interior surface of guide tube 34 defines an arcuate contacting surface which permits the wire advanced therethrough to bend causing the wire stock to assume a generally sinusoidal shape. The individual die elements 35 may be positioned in any desired arrangement. For example, as shown in FIG. 4, the die elements 35a, 35e and 35f may be positioned so as not to deflect the guide tube 34 from the axis defined by housing 32. Die elements 35b may urge the guide tube to one side of the longitudinal axis of the housing 32 while die elements 35c and 35d may urge the guide tube 34 to the other side the longitudinal axis of housing 32. Determining the number of die elements necessary to straighten a wire of a given diameter as well as the necessary positioning of the die elements within the housing are within the purview of those skilled in the art.

Figure 5:
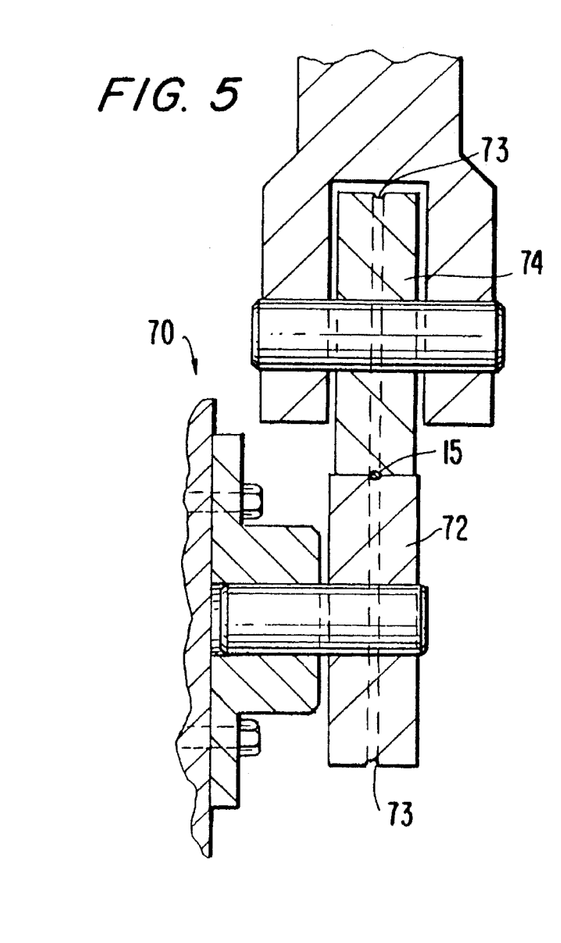
FIG. 5 is a cross-sectional view along line 5—5 of FIG. 4.

Drive mechanism 70 draws the stock wire 15 through the straightening station 30. As best seen in FIG. 5, drive mechanism 70 includes driven wheel 72 and idler wheel 74. Motor 71 is operably connected to and continuously drives wheel 72. Wheels 72 and 74 each have a circumferential groove 73 formed therein. Grooves 73 are semi-circular in shape and are precisely machined to match the size of the stock wire 15. Tensioning means 71 urges idler wheel 74 into contact with stock wire 15, which is placed between wheels 72 and 74. The wheels 72, 74 engage stock wire 15 with sufficient frictional force to pull it through straightening station 30. Wheels 72 and 74 are removable, and can be replaced with similar pairs of wheels, each pair having grooves precisely machined to accommodate a different size wire. The speed at which motor 71 drives wheel 72 is electronically controlled in response to signals generated by the sensing station 40 as described below. Generally, however, motor 71 will cause stock wire 15 to advance at a rate of from about 10 mm/sec to about 16 mm/sec.

After passing through drive mechanism 70, stock wire 15 passes through sensing station 40 which monitors the position of stock wire 15 and regulates the speed at which drive mechanism 70 operates. Sensing station 40 includes a dancing arm 42 which is pivotally mounted to support wall 11 at point 41 and has a roller 44 mounted thereon. Stock wire 15 is placed below and supports roller 44. Arm 42 is free moving, and will move due to the action of gravity or the motion of stock wire 15. Thus, dancing arm 42 will be lowered by slackening of stock wire 15 and will be raised as stock wire 15 becomes taut. Sensors 45, 46, 47 and 48 are provided to monitor the position of dancing arm 42. When sensor 46 detects the presence of dancing arm 42 indicating that stock wire 15 has become too slack, sensor 46 electronically signals drive mechanism 70 and the speed at which motor 71 operates is decreased to reduce the slack in stock wire 15. Similarly, when sensor 47 detects the presence of dancing arm 42 indicating that stock wire 15 has become too taut, sensor 47 electronically signals drive mechanism 70 and the speed at which motor 71 operates is increased to create more slack in on stock wire 15. Sensors 45 and 48 operate to shut down the apparatus 10 in the event sensors 46 and 47 fail to adequately control the position of dancing arm 42.

After leaving sensor station 40, stock wire 15 is then engaged by drive mechanism 80 which controls the position of the stock wire 15 as it passes through cutting station 60. The structure and operation of drive mechanism 80 is the same as that of drive mechanism 70 described above with the exception that drive wheel 82 is operatively connected to a stepper motor 85 rather than to a continuous drive motor. Stepper motor 85 advances the stock wire 15 to a first, drilling position and to a second, cutting position. The actual distance that the stepper motor will move the stock wire to achieve the drilling and cutting position may be the same or different and will depend upon the desired final length of the needle blank.

Figure 7:
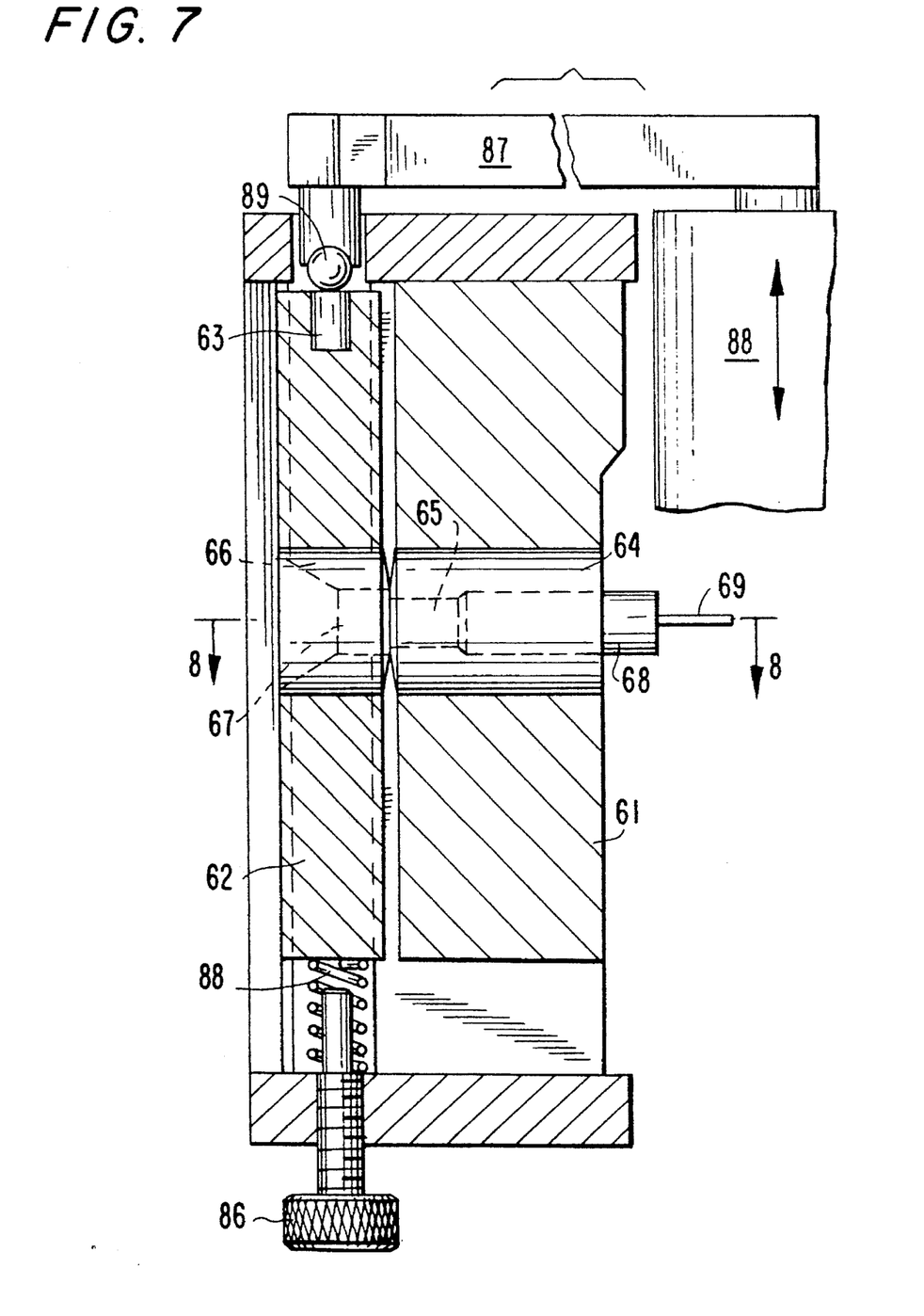
FIG. 7 is a cross-sectional view of the cutting station of a needle blank forming apparatus in accordance with the present invention.
Figure 8:
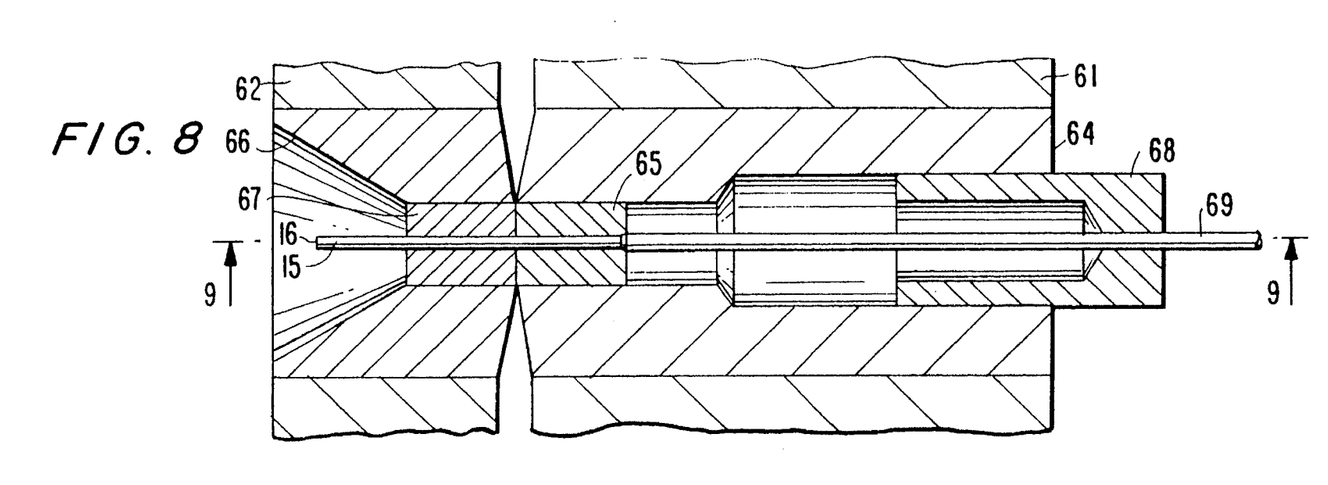
FIG. 8 is a cross-sectional view along lines 8—8 of FIG. 7.
Figure 9:
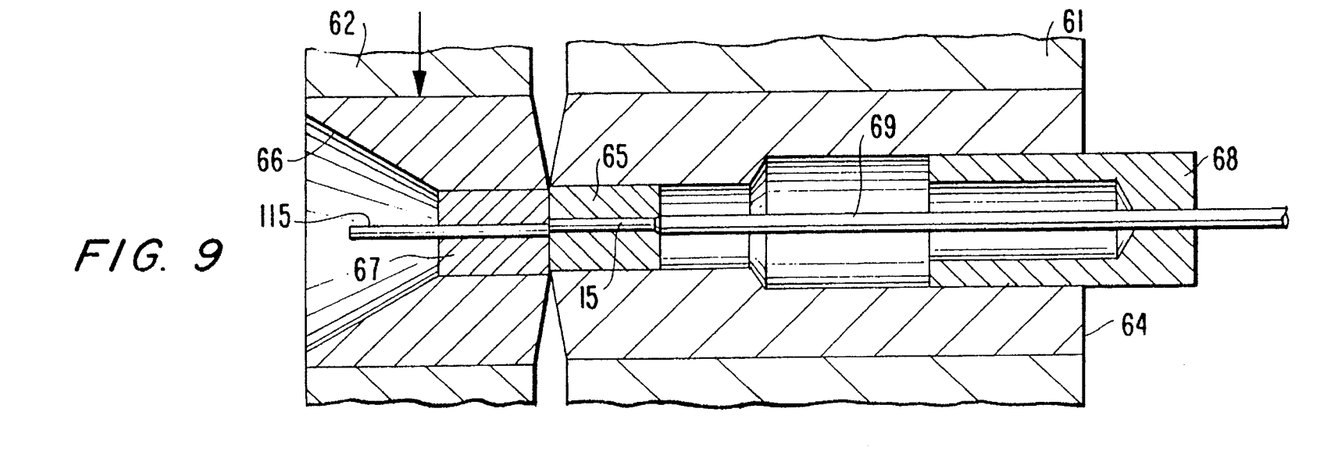
FIG. 9 is a cross-sectional view along lines 9—9 of FIG. 8 after activation of the cutting station.

From drive mechanism 80, the stock wire 15 enters cutting station 60. As best seen in FIGS. 7–9, the cutting station 60 includes a stationary housing 61 and a moveable housing 62. Stationary die 64 is received and removably mounted within stationary housing 61 and moveable die 66 is received and removably mounted within moveable housing 62. Each die 64, 66 includes a carbide insert, 65, 67, respectively. Stationary die 66 also includes a bushing 68. A rigid guide tube 69 passes through bushing 68 and guides stock wire 15 to the central bore of insert 67. The rigid guide tube 69 is preferably hypodermic tubing made from stainless steel. A central bore is formed in each insert 65, 67 and is configured and dimensioned to receive stock wire 15 with the minimal amount of clearance that will allow stock wire 15 to slide through. The clearance between the central bores in inserts 65, 67 and stock wire 15 is preferably no more than 0.0010 inches, most preferably between 0.0003 and 0.0006 inches clearance over the diameter of stock wire 15.

In order to form needle blanks of other diameters, interchangeable matching pairs of fixed and moveable dies may be provided which have longitudinal bores formed therein with diameters corresponding to those of the other diameter wires to be formed into needle blanks. In order to assure that the longitudinal bore of movable die 66 is aligned with that of fixed die 64, adjusting screws 84 are provided on to raise or lower the stationary die.

Movement of the moveable die 66 is provided by lever arm 87. One end of lever arm 87 contacts moveable housing 62. Bearing 89 provided on lever arm 87, contacts a Teflon insert 63 in moveable housing 62 to allow removal of moveable housing 62 by sliding it out from under the lever arm 87. The other end of lever arm 87 contacts the piston 88 of an electromechanical device. As piston 88 moves upward, lever arm 87 pivots on support wall 13 causing downward movement of movable housing 62, thereby shearing stock wire 15 between movable die 66 and stationary die 64. Moveable housing 62 is returned to its original position by spring 88. The force applied by spring 88 may be adjusted via knob 86.

Drilling system 50 provides means for forming a bore in the stock wire 15 prior to activation of the cutting station 60. The forming means may comprise any of the known types of bore-forming devices such as drill machinery, electric discharge machining devices and electron beam machinery devices. Preferably, however, a laser is used to form the bore in stock wire 15. The laser may be of any type which provides a sufficiently narrow laser beam of sufficient energy to achieve drilling of the needle material. Suitable lasers are known to those skilled in the art. The laser is aligned such that the beam 55 travels along a line defined by the longitudinal axis of the central bore in moveable die 66. This assures that when fired, the laser beam strikes the stock wire 15 at the center thereof.

Control means coordinates the activation of drive mechanism 80, the laser and cutting station 60 such that the stock wire is drilled prior to being cut into needle blanks. While the various operations may be activated by manual control means, preferably the operations of apparatus 10 are controlled by a programmable control system (not shown) of a known type. A particularly useful sequence of operation which may be employed to form drilled needle blanks involves four steps. First, the stepper motor 85 of drive mechanism 80 advances the stock wire 15 a predetermined distance to the drilling position. When in the drilling position, the lead end 16 of stock wire 15 should extend out of the carbide insert 67 of moveable die 66, so that the laser does not affect the carbide insert. The lead end of the stock wire should not, however extend out an amount sufficient to affect the centrality of the bore. Next, the laser is fired to form a bore in the lead end 16 stock wire 15. Then, the stepper motor 85 of drive mechanism 80 is again activated to advance stock wire 15 a predetermined distance to the cutting position. Finally, the cutting station 60 is activated to provide a drilled needle blank 115 of a desired length. When the cycle is repeated, the first step not only advances the stock wire to the proper drilling position, but also ejects the needle blank 115 formed in the previous cycle.

Figure 6:
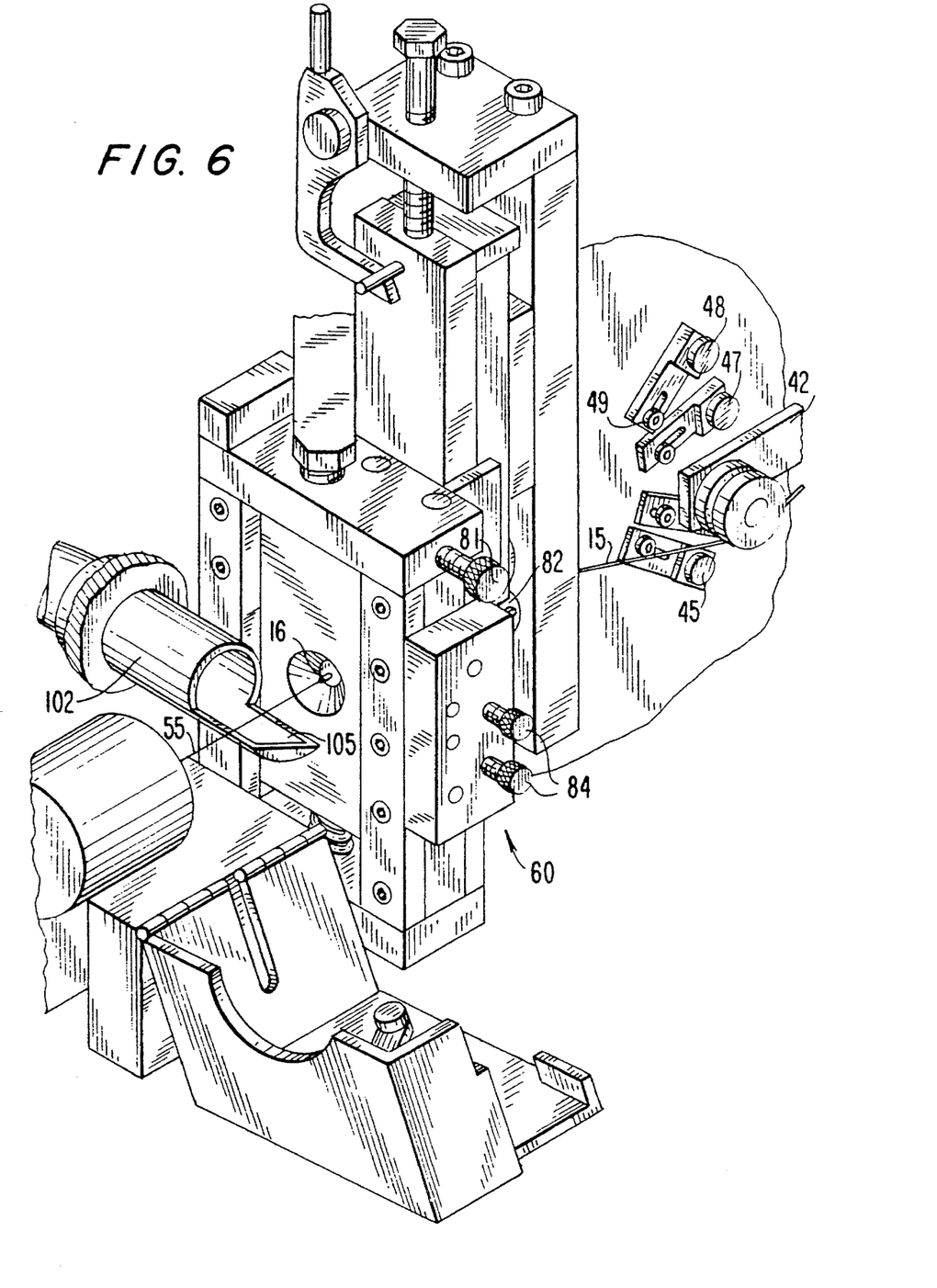
FIG. 6 is a perspective view of drilling and cutting stations of a needle blank forming apparatus in accordance with the present invention.

Once ejected, the needle blank can be received by a collecting means. The collecting means may simply be a box for collecting the ejected needle blanks. Alternatively, as best seen in FIGS. 1 and 6, the collecting means includes a vacuum tube 102 having a receiving portion 105 which catches the needle blanks as they are ejected. Tube 102 is connected to a vacuum source (not shown). When a needle blank falls into receiving portion 105 it is sucked into tube 102 to remove it from the area of the cutting and drilling stations. The needle blank may be deposited into receptable means such as a container or hopper (not shown) for storage or transport.

The apparatus of this invention can be adapted to prepare drilled needle blanks from any coiled stock material of any diameter. Preferably, the device is employed to prepare drilled needle blanks from stock wire having a diameter of 0.017 inches or less.

While the invention has been particularly shown and described with reference to the preferred embodiments, it will be understood by those skilled in the art that various modifications and changes in form and detail may be made therein without departing from the scope and spirit of the invention. Accordingly, modifications such as those suggested above but not limited thereto, are to be considered within the scope of the invention.

What is claimed is:

1. An apparatus for producing a drilled needle blank of predetermined length from a supply of stock wire which comprises:

a wire transporter to advance the stock wire and the leading end surface thereof in a distal direction to a drill station;

a drill positioned at the drill station to form a suture attachment portion in said leading end surface of the stock wire; and a wire cutter positioned proximal to the drill station to cut the stock wire at the predetermined length to produce the drilled needle blank.

2. An apparatus as in claim 1 wherein the drill is a laser.

3. An apparatus as in claim 2 wherein the laser fires a beam substantially in alignment with the longitudinal axis of the stock wire.

4. An apparatus as in claim 1 wherein the wire transporter includes:

a first wheel having a circumferential groove formed therein;

a second wheel having a circumferential groove formed therein, the first and second wheels being positioned adjacent one another such that the said grooves form a generally circular opening between the wheels, the second wheel being biased toward the first wheel such that the stock wire placed between the wheels is frictionally engaged by the wheels; and a motor to rotate the first wheel.

5. An apparatus as in claim 1 wherein the wire cutter includes:

a stationary die having a longitudinal bore therein for receiving the stock wire;

a movable die having a longitudinal bore therein for receiving the stock wire;

means for moving the movable die relative to the stationary die whereby stock wire within the longitudinal bores is sheared.

6. An apparatus as in claim 1 further comprising a wire straightener positioned proximal to the wire cutter.

7. An apparatus as in claim 1 further comprising a wire cleaner positioned proximal to the wire cutter.

8. An apparatus as in claim 1 further comprising a programmable control system to coordinate activation of the wire transporter, the drill and the wire cutter.

9. A method for producing a drilled needle blank of predetermined length from a supply of stock wire comprising:

advancing the stock wire and the leading end surface thereof in a distal direction to a drill station;

forming a suture attachment portion in said leading end surface of the stock wire at the drill station; and cutting the stock wire proximal to the drill station at the predetermined length to produce the drilled needle blank.

10. A method as in claim 9 wherein the step of forming a suture attachment portion comprises applying laser energy to the stock wire.

11. A method as in claim 10 wherein the laser energy is applied to form a bore in the stock wire, the bore extending substantially parallel to the longitudinal axis of the stock wire.

12. A method as in claim 10 wherein the step of cutting the stock wire comprises:

providing a pair of dies each having a bore formed therethrough, the dies being movable between a first position wherein the bores are substantially aligned and a second position wherein the bores are not substantially aligned;

positioning the stock wire within the bores while the dies are in said first position; and moving said dies to said second position whereby the stock wire is cut.

13. A method as in claim 12 wherein the step of forming a suture attachment portion comprises firing a laser to form a bore in the end of the stock wire while the stock wire is positioned within the bores of the dies.

14. An apparatus for producing a drilled needle blank of predetermined length from stock wire of length greater than the predetermined length which comprises:

a wire transporter to advance the stock wire and the leading end surface thereof incrementally in a distal direction from a cutting station to a drill station;

a laser positioned at the drill station to form a bore in said leading end surface of the stock wire; and a wire cutter positioned at the cutting station to cut the stock wire at the predetermined length to produce the drilled needle blank.

15. An apparatus as in claim 14 wherein in the wire cutter includes:

a stationary die having a longitudinal bore therein for receiving the stock wire;

a movable die having a longitudinal bore therein for receiving the stock wire;

means for moving the movable die relative to the stationary die whereby stock wire within the longitudinal bores is sheared.

16. An apparatus as in claim 14 wherein the laser is positioned to form a bore which is substantially parallel to the axis of elongation of the stock wire.

17. An apparatus as in claim 14 further comprising a programmable controller to coordinate activation of the laser, wire cutter and wire transporter.

18. An apparatus as in claim 14 wherein the wire transporter includes a stepper motor.

* * * * *